(12) United States Patent
Miyama

(10) Patent No.: US 8,870,777 B2
(45) Date of Patent: Oct. 28, 2014

(54) ULTRASOUND DIAGNOSTIC APPARATUS

(75) Inventor: Koji Miyama, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 219 days.

(21) Appl. No.: 13/182,523

(22) Filed: Jul. 14, 2011

(65) Prior Publication Data

US 2012/0016242 A1 Jan. 19, 2012

(30) Foreign Application Priority Data

Jul. 14, 2010 (JP) .................. 2010-159470

(51) Int. Cl.
*A61B 8/06* (2006.01)
*A61B 8/08* (2006.01)
*A61B 8/13* (2006.01)

(52) U.S. Cl.
CPC ... *A61B 8/06* (2013.01); *A61B 8/13* (2013.01); *A61B 8/5269* (2013.01)
USPC ........... 600/454; 600/437; 600/440; 600/443; 600/447; 600/450; 382/131

(58) Field of Classification Search
CPC ........ A61B 5/0456; A61B 6/541; A61B 8/08; A61B 8/543; G01S 7/52034
USPC .......................... 600/437, 443, 447; 382/131
See application file for complete search history.

(56) References Cited

U.S. PATENT DOCUMENTS

| | | | |
|---|---|---|---|
| 5,921,931 A * | 7/1999 | O'Donnell et al. | 600/441 |
| 6,228,030 B1 * | 5/2001 | Urbano et al. | 600/443 |
| 8,029,444 B2 * | 10/2011 | Pedrizzetti et al. | 600/438 |
| 2003/0216644 A1 | 11/2003 | Hall | |
| 2005/0203395 A1 * | 9/2005 | Sui et al. | 600/437 |
| 2009/0326378 A1 * | 12/2009 | Lee et al. | 600/447 |
| 2010/0113930 A1 * | 5/2010 | Miyachi | 600/443 |
| 2010/0331694 A1 * | 12/2010 | Waki | 600/443 |

FOREIGN PATENT DOCUMENTS

| | | |
|---|---|---|
| CN | 1182357 A | 5/1998 |
| CN | 1257694 A | 6/2000 |
| CN | 1718164 A | 1/2006 |
| JP | H04236950 A | 8/1992 |
| JP | 05277111 | 10/1993 |
| JP | 07079974 | 3/1995 |

(Continued)

OTHER PUBLICATIONS

Richard Y. Chiao et al., "B-mode Blood Flow (B-Flow) Imaging," IEEE Ultrasonics Symposium, vol. 2, pp. 1469-1472 (2000).

*Primary Examiner* — Baisakhi Roy
(74) *Attorney, Agent, or Firm* — Armstrong Teasdale LLP

(57) ABSTRACT

An ultrasonic diagnosis apparatus includes a frame data generation device configured to generate a frame data of a blood flow image based on echo signals obtained by transmissions and receptions of ultrasonic waves on a same acoustic ray, a processed frame data generation device configured to generate a processed frame data using current data excluding an error data having a higher brightness, a faster blood speed, or a higher blood flow power than a brightness, a blood speed, or a blood flow power of standard data within pixel data corresponding to each other in a plurality of frame data at different time phases, and an image display control device configured to display a blood flow image based on the processed framed data.

5 Claims, 10 Drawing Sheets

(56) References Cited

FOREIGN PATENT DOCUMENTS

| JP | H09220228 A | 8/1997 |
| JP | H1075955 A | 3/1998 |
| JP | H10305036 A | 11/1998 |
| JP | H11267125 A | 10/1999 |
| JP | 2003528668 A | 9/2003 |
| JP | 2004-129967 | 4/2004 |
| JP | 2006116329 A | 5/2006 |
| JP | 2009183564 A | 8/2009 |
| JP | 2010-125203 | 6/2010 |

\* cited by examiner

ULTRASOUND DIAGNOSTIC APPARATUS

CROSS REFERENCE TO RELATED APPLICATIONS

This application claims the benefit of Japanese Patent Application No. 2010-159470 filed Jul. 14, 2010, which is hereby incorporated by reference in its entirety.

BACKGROUND OF THE INVENTION

The embodiments described herein relate to an ultrasonic diagnostic apparatus for displaying a blood flow image.

For blood flow images, a B-flow image, a color Doppler image, and a power Doppler image are listed for example. Those blood flow images are generated based on echo signals obtained from multiple transmitting/receiving of ultrasonic waves on the same acoustic ray.

For example, brightness of moving objects is displayed higher in the B-flow image so that a high bright image momentarily may be displayed if a subject moves while the ultrasonic waves transmit/receive or an ultrasonic probe moves. Also, in the B-flow image close to a heart, as tissues around the heart move, there may be frames in that such parts are shown with high brightness along beating of the heart. Such images are difficult to be seen when frames have momentary high brightness in the blood flow image. Further, it is also difficult to be seen in the color Doppler image and the power Doppler if there are frames momentarily showing high blood speed and high blood flow power.

BRIEF DESCRIPTION OF THE INVENTION

A first aspect provides an ultrasonic diagnosis apparatus including: a frame data generation device for generating a frame data of a blood flow image based on echo signals obtained by multiple times of transmitting/receiving of an ultrasonic wave on the same acoustic ray; a processed frame data generation device for generating a processed frame data using a current data with the exception of an error data that is higher brightness, faster blood speed, or higher blood flow power than a standard data within pixel data corresponding each other in the plurality of frame data at different time phases; and an image display control device for displaying a blood flow image based on the processed framed data.

A second aspect is the ultrasonic diagnosis apparatus of the first aspect, wherein the processed frame data generation device determines a maximum brightness data or a predetermined number of data in descending order of brightness as an estimated error data, and selects the standard data from a data with the exception of the estimated error data.

A third aspect is the ultrasonic diagnosis apparatus of the second aspect, wherein the error data has a higher brightness with a predetermined brightness data than the standard data in the estimated error data.

A fourth aspect is the ultrasonic diagnosis apparatus of the first aspect, wherein the processed frame data generation device determines a maximum blood speed data or a predetermined number of data in descending order of blood flow as an estimated error data, and selects the standard data from a data with the exception of the estimated error data.

A fifth aspect is the ultrasonic diagnosis apparatus of the fourth aspect, wherein the error data has a faster velocity data with a predetermined velocity than the standard data in the estimated error data.

A sixth aspect is the ultrasonic diagnosis apparatus of the first aspect, wherein the processed frame data generation device determines a maximum blood flow power data or a predetermined number of data in descending order of blood flow power as an estimated error data, and selects the standard data from a data with the exception of the estimated error data.

A seventh aspect is the ultrasonic diagnosis apparatus of the sixth aspect, wherein the error data is a data that is higher blood flow power with a predetermined blood flow power than the standard data in the estimated error data.

An eighth aspect provides the ultrasonic diagnosis apparatus including: a frame data generation device for generating a frame data of a blood flow image based on echo signals obtained by a plurality of transmitting/receiving of an ultrasonic wave on the same acoustic ray; a processed frame data generation device for generating a processed frame data based on the frame data; and an image display control device for displaying a blood flow image based on the processed framed data, wherein the processed frame data generation device determines a maximum brightness data or a predetermined number of data in descending order of brightness as an estimated error data of pixel data corresponding each other in the plurality of frame data at different time phases; uses a data of a current frame as the data for the processed frame data when the estimated error data is not a data of the current frame; and generates the processed frame data using the data of the current frame with the exception of an error data that is brighter than the standard data of the estimate error data when the estimated error data is the data of the current frame.

A ninth aspect is the ultrasonic diagnosis apparatus of the eighth aspect, wherein the error data has a higher brightness with a predetermined brightness data than the standard data in the estimated error data.

A tenth aspect provides the ultrasonic diagnosis apparatus of the second aspect, including: a frame data generation device for generating a frame data of a blood flow based on echo signals obtained by a plurality of transmitting/receiving of an ultrasonic wave on the same acoustic ray; a processed frame data generation device for generating a processed frame data based on the frame data; and an image display control device for displaying a blood flow image based on the processed framed data, wherein the processed frame data generation device determines a maximum blood speed data or a predetermined number of data in descending order of blood speed as an estimated error data of pixel data corresponding each other in the plurality of frame data at different time phases; uses a data of a current frame as the data for the processed frame data when the estimated error data is not a data of the current frame; and generates the processed frame data using the data of the current frame with the exception of an error data that is higher blood speed than the standard data of the estimate error data when the estimated error data is the data of the current frame.

An eleventh aspect is the ultrasonic diagnosis apparatus of the tenth aspect, wherein the error data has a faster velocity data with a predetermined velocity than the standard data in the estimated error data.

A twelfth aspect provides the ultrasonic diagnosis apparatus including: a frame data generation device for generating a frame data of a blood flow based on echo signals obtained by a plurality of transmitting/receiving of an ultrasonic wave on the same acoustic ray; a processed frame data generation device for generating a processed frame data based on the frame data; and an image display control device for displaying a blood flow image based on the processed framed data, wherein the processed frame data generation device determines a maximum blood flow power data or a predetermined number of data in descending order of blood flow power as an estimated error data of pixel data corresponding each other in the plurality of frame data at different time phases; uses a data of a current frame as the data for the processed frame data when the estimated error data is not a data of the current frame; and generates the processed frame data using the data of the current frame with the exception of an error data that is higher blood speed than the standard data of the estimate error data when the estimated error data is the data of the current frame.

A thirteenth aspect is the ultrasonic diagnosis apparatus of the twelfth aspect, wherein the error data has a data that is higher blood flow power with a predetermined blood flow power than the standard data in the estimated error data.

A fourteenth aspect is the ultrasonic diagnosis apparatus of any of the eighth to the thirteenth aspect, wherein the processed frame data generation device selects the standard data from data with the exception of the estimated error data of pixel data corresponding each other in the plurality of frame data.

A fifteenth aspect is the ultrasonic diagnosis apparatus of the second to the fourteenth aspect, further including an estimated error data number input device for inputting the number that is the estimated error data.

A sixteenth aspect provides an ultrasonic diagnosis apparatus including: a frame data generation device for generating a frame data of a blood flow based on echo signals obtained by a plurality of transmitting/receiving of an ultrasonic wave on the same acoustic ray; a processed frame data generation device for generating a processed frame data using a data whose brightness, blood speed or blood flow power are a median of pixel data corresponding each other in the plurality of frame data at different time phases; and an image display control device for displaying a blood flow image based on the processed framed data.

A seventeenth aspect is the ultrasonic diagnosis apparatus of any of the first to the sixteenth aspect, wherein the plurality of frame data at different time phases are frame data from a current data to a data of a predetermined number of frames back from the current data.

An eighteenth aspect is the ultrasonic diagnosis apparatus of any of the first to the seventeenth aspect, further including a frame number input device for inputting number of frame data that is an object of generating the processed frame data.

A nineteenth aspect is the ultrasonic diagnosis apparatus of any of the first to the eighteenth aspect, wherein the frame data is a raw data before scan-converted by a scan converter.

A twentieth aspect is the ultrasonic diagnosis apparatus of any of the first, second, third, eighth, or ninth aspects, wherein the blood flow image is a B-flow image.

A twenty-first aspect is the ultrasonic diagnosis apparatus of any of the first, fourth, fifth, sixth, seventh, tenth, eleventh, twelfth, or thirteenth aspects, wherein the blood flow image is a color Doppler image.

A twenty-second aspect is the ultrasonic diagnosis apparatus of any of the first, sixth, seventh, twelfth, or thirteenth aspects, wherein the blood flow image is a power Doppler image.

According to the above-mentioned aspects, by displaying the blood flow image based on the processed frame data with the exception of the error data of pixel data corresponding each other in the plurality of frame data, display of images momentarily showing high brightness, fast blood speed, or high blood flow power can be prevented. Further, the processed B-flow frame data includes the current data with the exception of the error data so that the blood flow image without losing the condition of blood flow can be displayed.

According to the above-mentioned aspects, when the estimated error data is not the data of the current frame of pixel data corresponding each other in the plurality of frame data, the data of the current frame is used for the data of the processed frame data, while when the estimated error data is the data of the current frame, the data of the current frame with the exception of the error data is used for the data of the processed frame data. As a result, the blood flow image based on the processed frame data with the exception of the error data is displayed so that it can prevent images from displaying momentary high brightness, fast blood speed, or high blood flow power. Further, the processed B-flow frame data includes the current data with the exception of the error data so that the B-flow image without losing the condition of blood flow can be displayed.

Moreover, according to the above-mentioned aspects, display of images momentarily showing high brightness can be prevented by displaying the blood flow image based on the processed frame data using the data that the brightness, the blood speed, or the blood flow power is the median.

Further objects and advantages of the embodiments described herein will be apparent from the following description of embodiments of the invention as illustrated in the accompanying drawings.

DETAILED DESCRIPTION OF THE INVENTION

Figure 1:
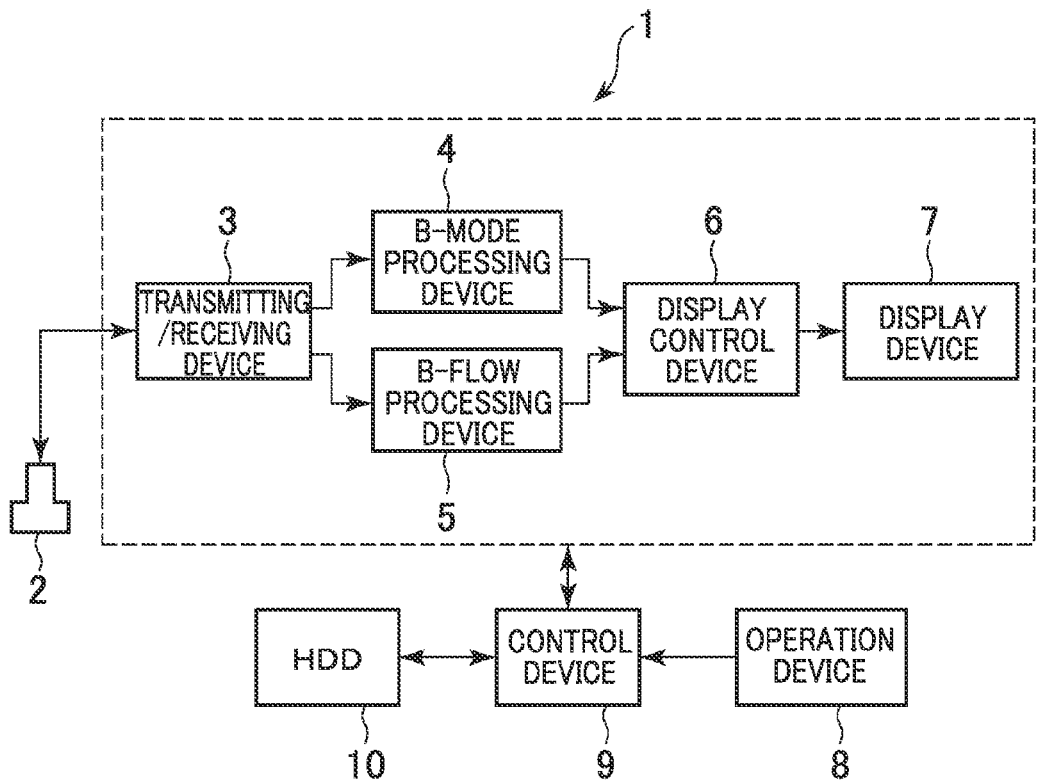
FIG. 1 is a block diagram showing one example of schematic configuration of the first embodiment of the ultrasonic diagnostic apparatus.

Embodiments of the invention are explained below referring to FIG. 1 through FIG. 7. An ultrasonic diagnostic apparatus 1 includes an ultrasonic probe 2, transmitting/receiving device 3, a B-mode processing device 4, a B-flow processing device 5, a display control device 6, a display device 7, an operation device 8, a control device 9, and HDD (Hard Disc Drive) 10.

The ultrasonic probe 2 has a plurality of ultrasonic transducers placed as an array (not shown) and the ultrasonic transducers transmit ultrasonic waves to a subject and receive reflected echo signals.

The transmitting/receiving device 3 drives the ultrasonic probe 2 under a predetermined transmitting condition to scan the scanning surface with an ultrasonic beam in the order of acoustic rays. The transmitting/receiving device 3 drives the ultrasonic probe 2 by a control signal from the control device 9. The transmitting/receiving device 3 drives the ultrasonic probe 2 to execute multiple transmitting and receiving of ultrasonic waves on the same acoustic ray.

The transmitting/receiving device 3 executes a signal processing, such as phasing addition, on the echo signal received by the ultrasonic probe 2, and outputs the signal-processed echo data to the B-mode processing device 4 and the B-flow processing device 5.

The B-mode processing device 4 generates a B-mode data by a predetermined process, such as a logarithmic compression process or an envelope detection process, on the data output from the transmitting/receiving device 3. The B-mode data is a data corresponding to the brightness of respective pixels. The B-mode data for one frame is referred as a B-mode frame data BFD. The B-mode frame data BFD includes a B-mode data of each acoustic ray for one frame. The B-mode frame data BFD output from the B-mode processing device is input to the display control device 6.

The B-flow processing device 5 performs the B-flow processing on the echo signal obtained from multiple transmitting/receiving of ultrasonic waves on the same acoustic ray and generates the B-flow data. The B-flow data is a data corresponding to the brightness of respective pixels. The B-flow data for one frame is referred as a B-flow frame data ffd. Thus, the B-flow processing device 5 performs generation of the B-flow frame data ffd (B-flow frame data generation function). The B-flow frame data ffd includes the B-flow data of each acoustic ray for one frame. The B-flow frame data ffd output from the B-flow processing device 5 is input to the display control device 6. The B-flow frame processing device 5 is one example of embodiments of the frame data generation device. The B-flow image displayed based on the B-flow data is one example of embodiments of the image of the blood flow, and the B-flow frame data ffd is one example of embodiments of the frame data of an image of the blood flow.

Figure 2:
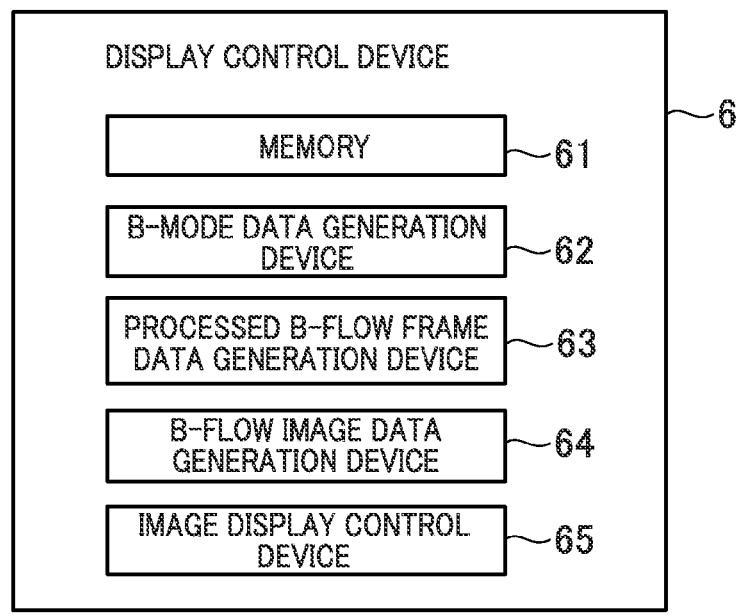
FIG. 2 is a block diagram showing the configuration of the display control device in the ultrasonic diagnostic apparatus shown in FIG. 1.

The display control device 6 includes, as shown in FIG. 2, a memory 61, a B-mode data generation device 62, a processed B-flow frame data generation device 63, a B-flow image data generation device 64, and an image display control device 65. The memory 61 includes a semiconductor memory, such as RAM (Random Access Memory) or ROM (Read Only Memory). The B-mode frame data BFD or the B-flow frame data ffd are stored in the memory 61, for example. The B-mode frame data BFD and the B-flow frame data ffd can be stored in the HDD 10.

The B-mode image data generation device 61 generates a B-mode image data by scan-converting the B-mode frame data BFD with a scan converter.

The processed B-flow frame data generation device 63 generates a processed B-flow frame data FFD using the current data with the exception of an error data that is higher brightness than a standard data from pixel data corresponding each other in the plurality of B-flow frame data ffd at different time phases (processed B-flow frame data generating function). The detail will be explained later. The processed B-flow frame data generation device 63 is one example of embodiments of the processed frame data generation device. Also, the processed B-flow frame data FFD is one example of embodiments of the processed frame data.

The B-flow image data generation device 64 generates a B-flow image data by scan-converting the processed B-mode frame data FFD with a scan converter.

The image display control device 65 adds the B-mode image data and the B-flow image data and displays an ultrasonic image combined of a B-mode image and a B-flow image (image display function). That is, in this embodiment, a blood flow image that is the B-flow image is displayed at the display 7 after it is combined with the B-mode image. The image display control device 65 is one example of embodiments of the image display control device.

The display device 7 includes LCD (Liquid Crystal Display) or CRT (Cathode Ray Tube), for example. The operation device 8 includes a keyboard or a pointing device (not shown) for an operator to input commands or information. With the operation device 8, the operator inputs the number of frame data or of estimated error data that is the object of generation of the processed B-flow frame data FFD as explained later. The operation device 8 is one example of embodiments of the frame number inputting device or estimated error data number inputting device.

The control device 9 includes CPU (Central Processing Unit). The control device 9 reads out a control program stored in the HDD 10 and executes functions including the B-flow frame data generating function, the processed B-flow frame data generating function, and the image display function at respective devices of the ultrasonic diagnosis apparatus.

The operation of the ultrasonic diagnosis apparatus 1 in this embodiment is explained. The B-mode processing device 4 generates a B-mode frame data BFD and the B-flow processing device 5 generates a B-flow frame data ffd based on the echo signal obtained by transmitting/receiving of the ultrasonic waves through the ultrasonic probe 2. Then, the B-mode frame data BFD and the B-flow frame data ffd are stored in the memory 61.

The B-mode image data generation device 62 generates a B-mode image data based on the B-mode frame data BFD. Meanwhile, the processed B-flow frame data generation device 63 generates a processed B-flow frame data FFD based on the B-flow frame data ffd. The generation of the processed B-flow frame data FFD is explained in detail based on a flow chart in FIG. 3.

Figure 3:
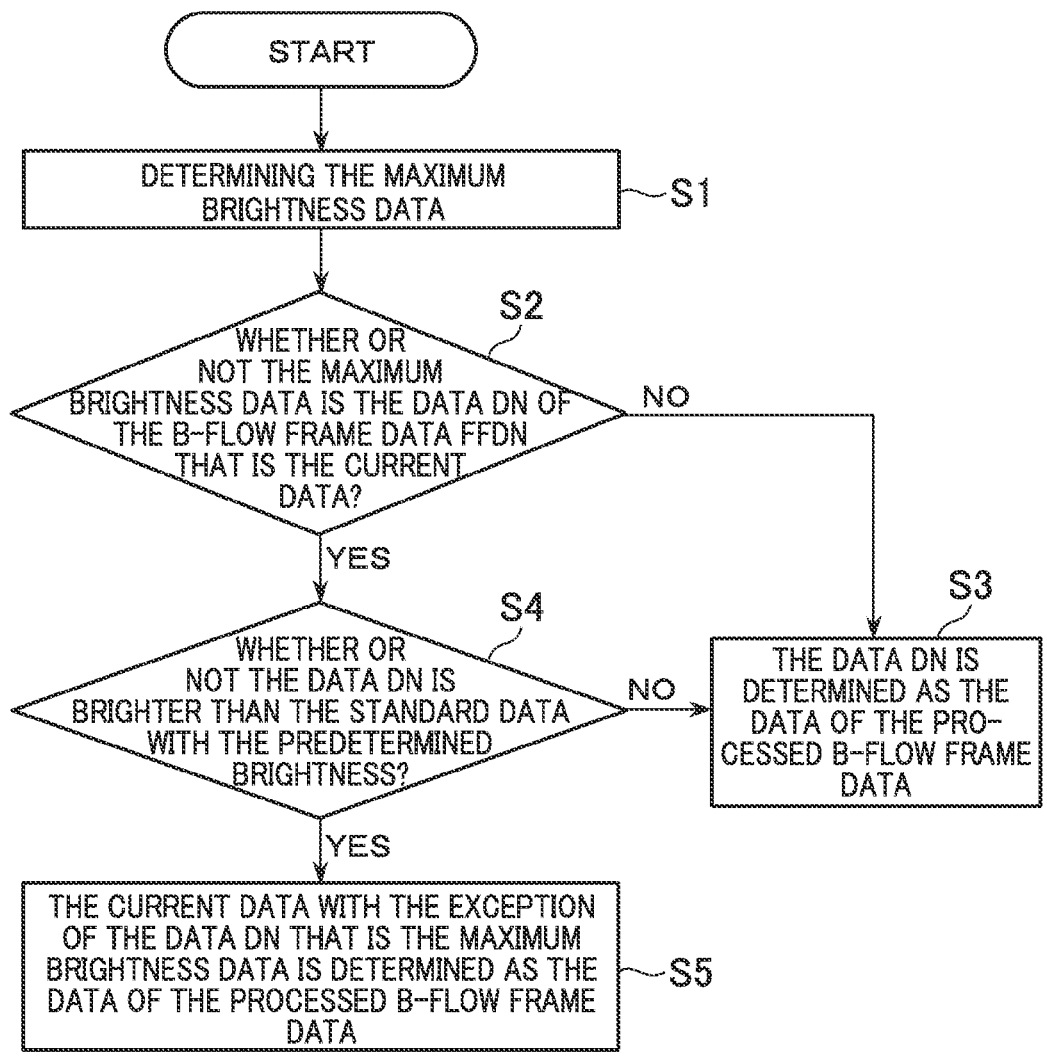
FIG. 3 is a flow chart showing the process for generating the processed B-flow frame data.
Figure 4:
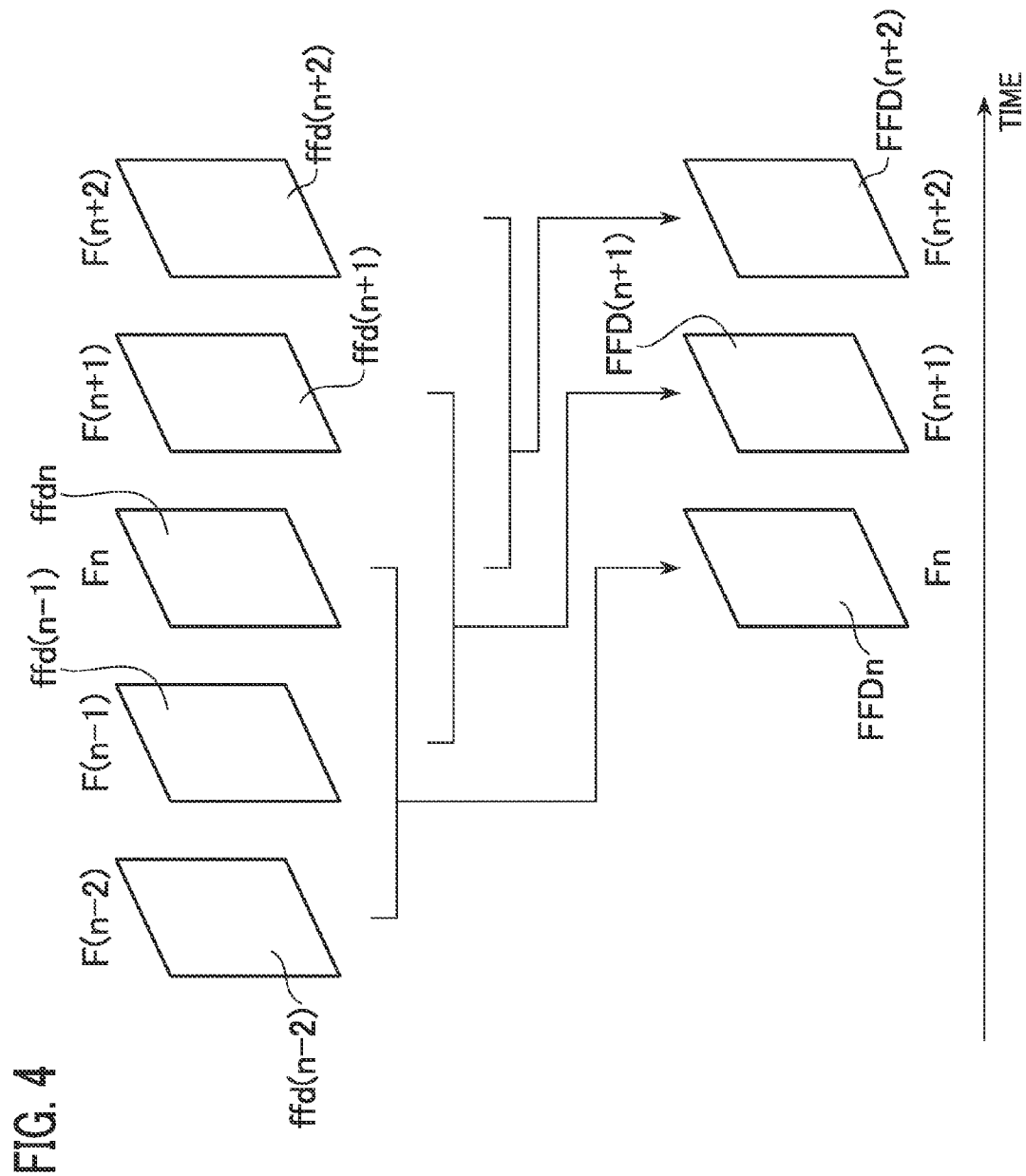
FIG. 4 is an explanation figure of generating the processed B-flow frame data based on the B-flow frame data.

As shown in FIG. 4, a B-flow frame data ffdn is obtained for the time phase of frame Fn and the ultrasonic image for the frame Fn is displayed. Steps S1 through S5 in FIG. 3 are performed on the B-flow frame data ffdn, ffd (n−1), ffd (n−2) of three frames that are the current frame Fn and two frames F (n−1) and F (n−2) back from the current frame Fn to generate the processed B-flow frame data FFDn.

Note that the number of frames that is the object of the process of the steps S1 through S5 and of the generation of the process B-flow frame data FFD is not limited to the three frames as explained above. And moreover, the number of frames can be set to an arbitrary number by an operator at the operation device 8.

The steps S1 through S5 are explained in reference to FIG. 3. The steps S1 through S5 are processes to one pixel, so the steps S1 through S5 are performed on each pixel to generate the processed B-flow frame data FFDn for one frame.

First in step S1, the processed B-flow frame data generation device 63 identifies a data having a maximum brightness (herein after, it is referred as "maximum brightness data") of the pixel data corresponding each other in the B-flow frame data ffdn, ffd (n−1), ffd (n−2) and defines the data as an estimated error data. In this embodiment, the number of estimated error data is "1", but a plurality of data can be defined as estimated error data in descending order of brightness as explained in a second variation embodiment. Also, the number of estimated error data can be modified by inputting through the operation device 8.

Next in step S2, the processed B-flow frame data generation device 63 determines whether or not the maximum brightness data is a data of the B-flow frame data of the current frame. Here, the current time phase is the frame Fn and the frame Fn is the current frame so that the processed B-flow frame data generation device 63 determines whether the maximum brightness data is a data of the B-flow frame data ffdn or not.

In the step S2, when the maximum brightness data is not determined as a data of the B-flow frame data ffdn (NO in step S2), it goes on to step S3. Meanwhile, when the maximum brightness data is determined as a data of the B-flow frame data ffdn (YES in step S2), it goes on to step S4.

Figure 5:
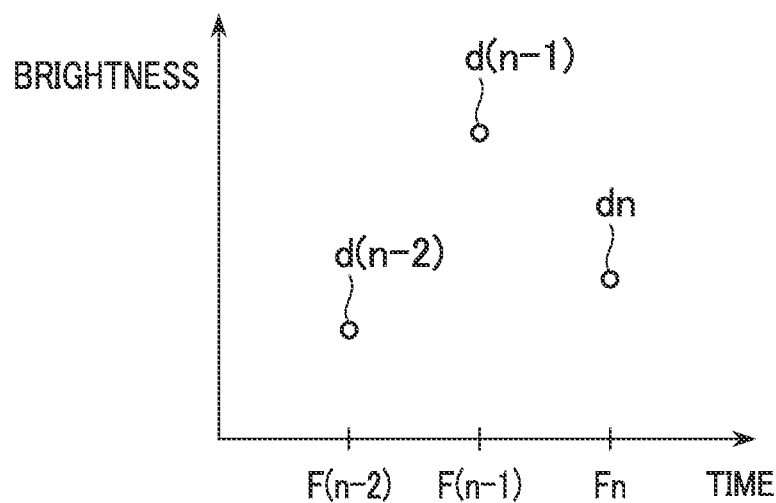
FIG. 5 is a figure for explaining the process of generating the processed B-flow frame data based on the B-flow frame data, which is an example of brightness of pixel data corresponding each other in the B-flow frame data for the three frames.
Figure 6:
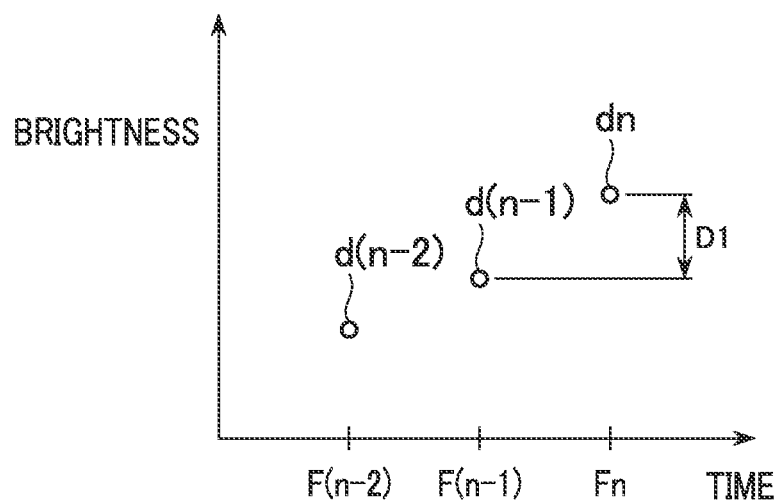
FIG. 6 is a figure for explaining the process of generating the processed B-flow frame data based on the B-flow frame data, which is another example of brightness of pixel data corresponding each other in the B-flow frame data for the three frames.
Figure 7:
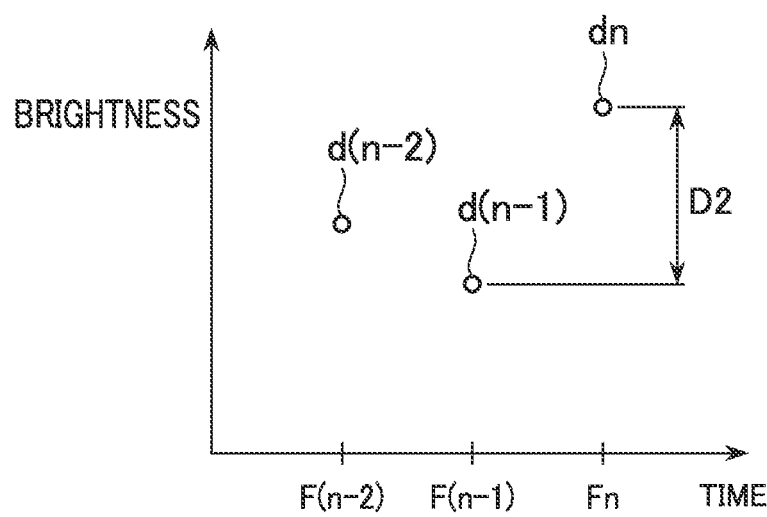
FIG. 7 is a figure for explaining the process of generating the processed B-flow frame data based on the B-flow frame data, which is another example of brightness of pixel data corresponding each other in the B-flow frame data for the three frames.

For example in FIG. 5 through FIG. 7, a data dn is a data of one pixel in the B-flow frame data ffdn of the frame Fn, a data d (n−1) is a data of one pixel in the B-flow frame data ffd (n−1) of the frame F (n−1), and a data d(n−2) is a data of one pixel in the B-flow frame data ffdd (n−2) of the frame F (n−2). In FIG. 5, the data d (n−1) is the maximum brightness data and the data dn is the maximum brightness data in FIG. 6 and FIG. 7. Therefore, it goes on to step S3 in the case shown in FIG. 5 and it goes on to step S4 in the case shown in FIG. 6 and FIG. 7.

In the step S3, the processed B-flow frame data generation device 63 determines the data of the frame Fn as the processed B-flow frame data FFDn. That is, the data dn is a data of the processed B-flow frame data FFDn. Meanwhile in the step S4, the processed B-flow frame data generation device 63 determines whether or not the data dn is a brighter data than the standard data with the predetermined brightness. The predetermined degree of brightness can be set by an operator through the operation device 8 and can be stored in the HDD 10 or the memory 61 in advance.

Here, the standard data is explained. The standard data is a data of the current frame with the exception of the maximum brightness data that is an estimated error data of the data dn, d(n−1), d(n−2) in the B-flow frame data ffdn, ffd (n−1), ffd (n−2). That is, the data d (n−1) of the frame f (n−1) is the standard data in this embodiment. Thus in the step S4, the processed B-flow frame data generation device 63 determines whether or not the data dn is brighter than the data d (n−1) with the predetermined brightness. In particular, the processed B-flow frame data generation device 63 determines whether or not the difference of brightness D between the data dn and the data d (n−1) is more than or equal to the predetermined threshold value DTH. The data dn that is determined that the difference of the data dn and the data d (n−1) is more than or equal to the threshold value DTH is referred as an "error data". That is, the error data is a data that is brighter than the standard data with the predetermined brightness.

In the step S4, when the difference of the data dn and the data d (n−1) is less than the threshold value DTH (NO in the step S4), it goes on to step S3. Meanwhile, the difference of the data dn and the data d (n−1) is more than or equal to the threshold value DTH (YES in the step S4), it goes on to step S5. In the step S5, the data d (n−1) that is the current data from data with the exception of the data dn that is the maximum brightness data determined as the error data is a data of the processed B-flow frame data FFDn.

In FIG. 6, the difference of brightness D1 of the data dn and the data d (n−1) is less than the threshold value DTH so that it goes on to the process of step S3. In step S3, the data dn is the data of the processed B-flow frame data FFDn.

In FIG. 7, the difference of brightness D2 of the data dn and the data d (n−2) is more than or equal to the threshold value DTH so that it goes on to the process of step S5. In step S5, the data d (n−1) is the data of the processed B-flow frame data FFDn.

The process B-flow frame data generation device 63 performs processes in steps S1 through S5 about the data of respective pixels and generates the processed B-flow frame data FFDn. In the processes of steps S1 through S5, when the data dn that is the current data is not an estimated error data (maximum brightness data), the data dn of the current frame is used as a data for the processed frame data FFDn so that current data with the exception of the error data is used. Meanwhile, even when the data dn is an estimated error data, the data of the current frame with the exception of the error data that is higher brightness than the standard data in the estimated error data (data dn in FIG. 6 and data d (n−1)) is used for a data for the processed frame data FFDn so that the current data with the exception of the error data is used similarly. Thus, the processed B-flow frame data generated by processing the steps S1 through S5 uses the current data with the exception of the error data.

When the processed B-flow frame data FFDn is generated, the B-flow image data generation device 64 generates the B-flow image data based on the processed B-flow frame data FFDn. After the B-flow image data is generated, the image display control device 65 combines the B-flow image data and the B-mode image data, and displays the ultrasonic image G.

For generating of the processed B-flow frame data FFD (n+1) of the frame F (n+1) next of the frame Fn, steps S1 through S5 in FIG. 3 are performed on the B-flow frame data ffdn (n+1), ffdn, ffd (n−1) of three frames that are the frame Fn (n+1) and two frames Fn and F (n−1) back from the frame Fn (n+1). Also for generating of the processed B-flow frame data FFD (n+2) of the frame F (n+2) next of the frame Fn (n+1), steps S1 through S5 in FIG. 3 are performed on the B-flow frame data ffd (n+2), ffd (n+1), ffdn of three frames that are the frame Fn (n+2) and two frames Fn (n+1) and Fn back from the frame Fn (n+2).

According to the above-mentioned ultrasonic diagnostic apparatus 1 of this embodiment, the B-flow image generated based on the processed B-flow frame data FFD with the exception of the error data is displayed so that it prevents images from displaying momentary high brightness on one or two frames, and easy viewable images can be displayed. Further, the processed B-flow frame data FFD includes the current data with exception of the error data so that the B-flow image clearly showing the blood flow can be displayed.

A variation of the first embodiment is explained. First of all, the first variation embodiment is explained. The standard data can be the central data of the corresponding pixel data in a plurality of B-flow frame data ffd as object for generating the processed B-flow frame data FFD. For example, in FIG. 6 the central data is the data d (n−1), and in the step S4, the data dn is determined whether or not it is a brighter data with a predetermined brightness than the data d (n−1) that is the standard data. In FIG. 7, the central data is the data d (n−2), and in the step S4, the data dn is determined whether or not it is a brighter data with a predetermined brightness than the data d (n−2) that is the standard data.

Figure 8:
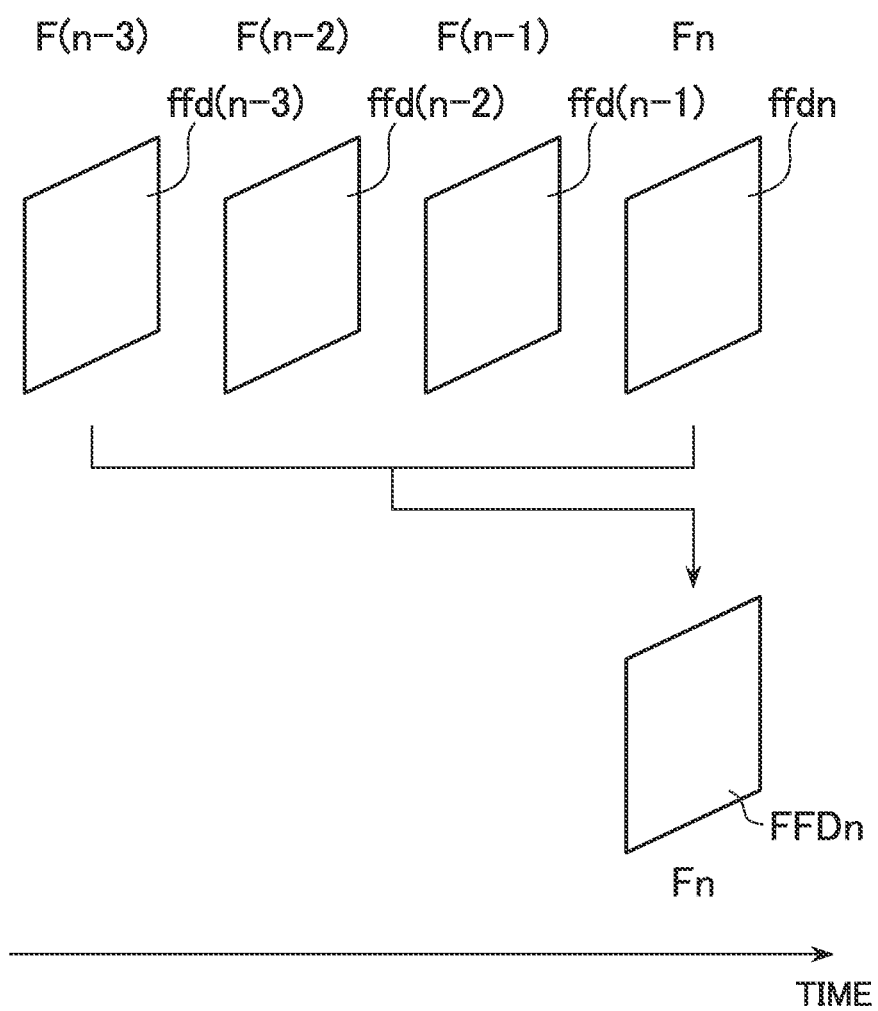
FIG. 8 is a figure for explaining the generation of the processed B-flow frame data based on the B-flow frame data in the second variation embodiment of the first embodiment.
Figure 9:
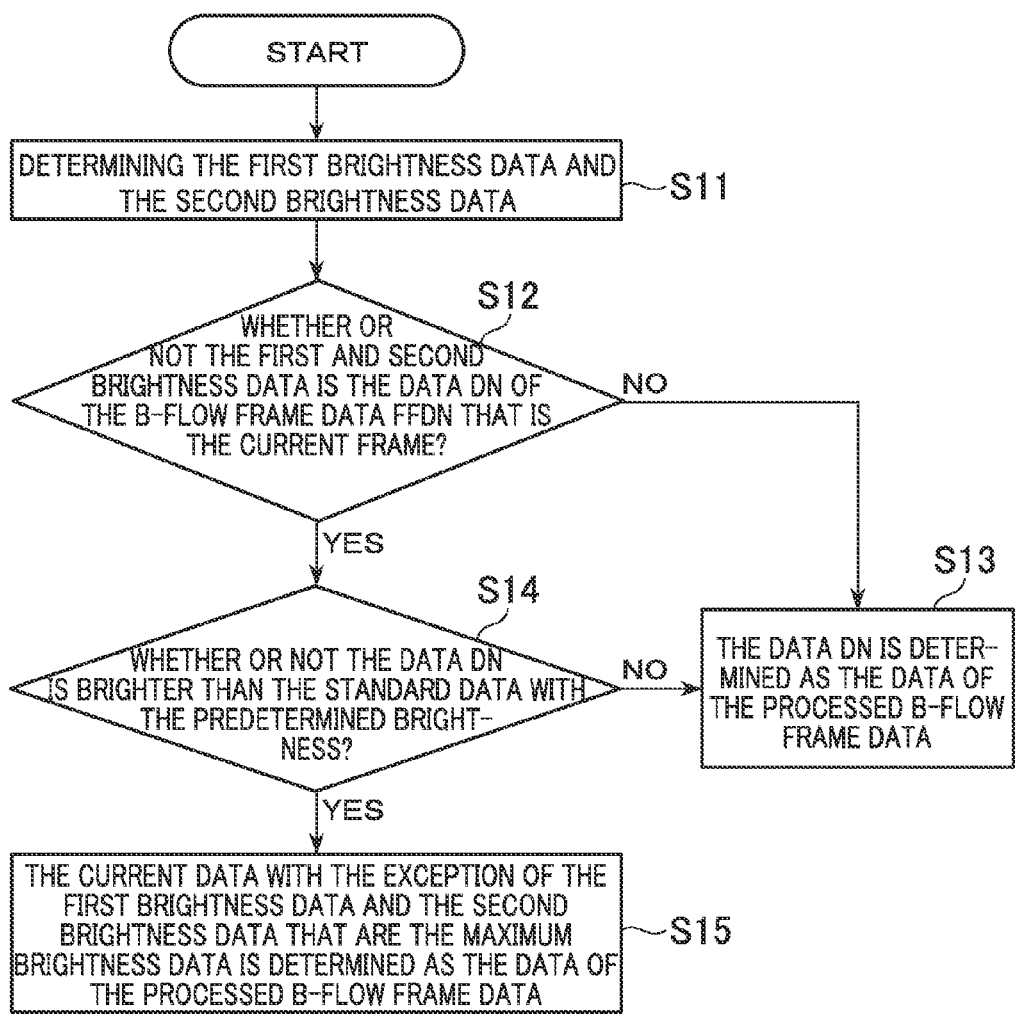
FIG. 9 is a flow chart showing the process for generating the processed B-flow frame data in the second variation embodiment of the first embodiment.

Next the second variation embodiment is explained. In the second variation embodiment, the number of frames that is an object for generating the processed B-flow frame data FFD is four frames. For example, as shown in FIG. 8, a case for displaying ultrasonic images for time phase of the frame Fn is explained based on the flow chart in FIG. 9. In steps S11 through S15 shown in FIG. 9, generating of the processed B-flow frame data FFDn is performed based on the B-flow frame data ffdn, ffd (n−1), ffd (n−2), ffd (n−3) of the frame Fn, F (n−1), F (n−2), F (n−3).

First in step S11, the processed B-flow frame data generation device 63 determines the maximum brightness data and the second highest brightness data from the pixel data corresponding to each other in the B-flow frame data ffdn, ffd (n−1), ffd (n−2), ffd (n−3) and they are considered as estimated error data. In this second variation embodiment, the maximum brightness data is referred as a first brightness data and the second highest brightness data is referred as a second brightness data. Thus, the first brightness data and the second brightness data are the estimated error data.

Next in step S12, the processed B-flow frame data generation device 63 determines whether or not either the first brightness data or the second brightness data is a data of the B-flow frame data of the current frame. The frame Fn is the current frame here, and the processed B-flow frame data generation device 63 determines whether or not either the first brightness data or the second brightness data is a data of the B-flow frame data ffdn.

In the step S12, when either the first brightness data or the second brightness data is not determined as the B-flow frame data ffdn (NO in step S12), it goes on to next step S13. Meanwhile, in step S12, when either the first brightness data or the second brightness data is determined as the B-flow frame data ffdn (YES in step S12), it goes on to next step S14.

Figure 10:
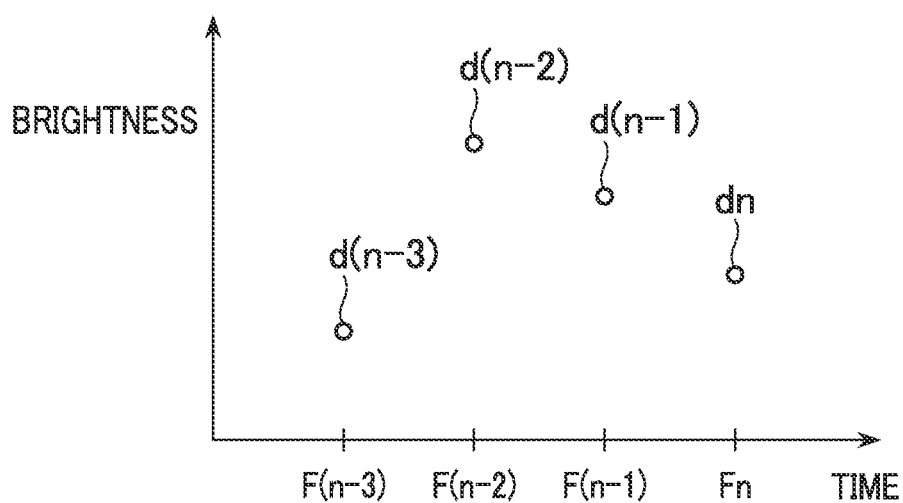
FIG. 10 is a figure for explaining the process of generating the processed B-flow frame data based on the B-flow frame data, which an example of brightness of pixel data corresponding each other in the B-flow frame data for the four frames in the second variation embodiment of the first embodiment.
Figure 11:
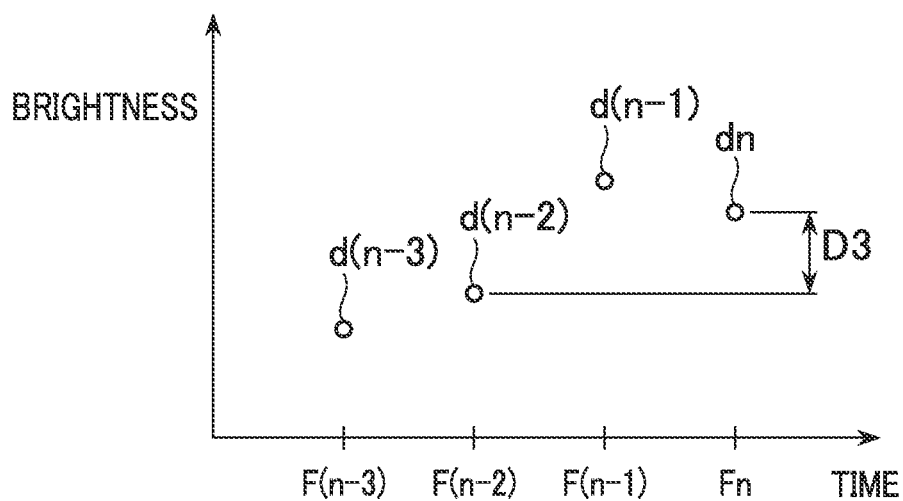
FIG. 11 is a figure for explaining the process of generating the processed B-flow frame data based on the B-flow frame data, which another example of brightness of pixel data corresponding each other in the B-flow frame data for the four frames in the second variation embodiment of the first embodiment.
Figure 12:
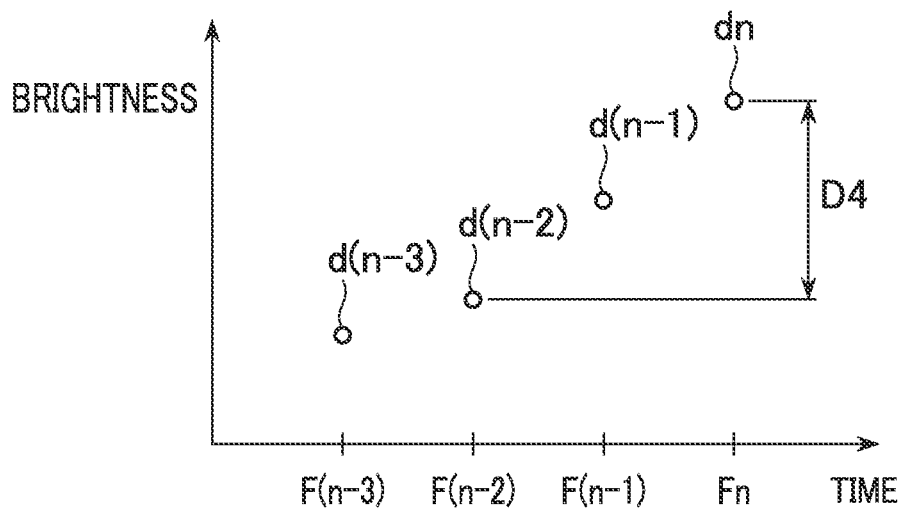
FIG. 12 is a figure for explaining the process of generating the processed B-flow frame data based on the B-flow frame data, which another example of brightness of pixel data corresponding each other in the B-flow frame data for the four frames in the second variation embodiment of the first embodiment.

As shown in FIG. 10, for example, when the data d (n−2) is the first brightness data and the data d (n−1) is the second brightness data, it goes on to step S13. On the other hand, as shown in FIG. 11, when the data d (n−1) is the first brightness data and the data dn is the second brightness data, and when the data dn is the first brightness data and the data d (n−1) is the second brightness data as shown in FIG. 12, it goes on to step S14.

In the step S13, the processed B-flow frame data generation device 63 defines the data of the frame Fn as the processed B-flow frame data FFDn like the process of the step S3. That is, the data dn is the processed B-flow frame data FFDn.

Meanwhile, in the step S14, the processed B-flow frame data generation device 63 determines whether or not the data dn is brighter than the standard data with the determined brightness.

The standard data is explained here. The standard data is the current frame data in the data with the exception of the first and second brightness data that is the estimated error data of the data dn, d (n−1), d(n−2), d(n−3). Thus, in FIG. 11, the standard data is the data d (n−2) and is data d (n−2) in FIG. 12. Therefore, in the example shown in FIG. 11, the processed B-flow frame data generation device 63 determines whether or not the difference D3 of brightness between the data dn and the data d (n−2) is more than the predetermined threshold value DTH so as to determine whether the brightness of the data dn is brighter with the predetermined brightness than the standard data or not. In the example shown in FIG. 12, in the step S14, the processed B-flow frame data generation device 63 determines whether or not the difference D4 of brightness between the data dn and the data d (n−2) is more than the predetermined threshold value DTH so as to determine whether the data dn is brighter with the predetermined brightness than the standard data or not.

In the step S14, when the data dn is determined to not be brighter with the predetermined brightness than the standard data (NO in step S14), it goes on to step S13. Meanwhile, in the step S14, when the data dn is determined to be brighter with the predetermined brightness than the standard data (YES in step S14), it goes on to step S15. In the step S15 the current data with the exception of the first and second brightness data is the processed B-flow frame data FFDn.

In FIG. 11, the difference D3 of the brightness between the data dn and the data d (n−2) is less than the threshold value DTH. Thus, it goes on to step S13 and the data dn is as the data of the processed B-flow frame data FFDn.

In FIG. 12, the difference D4 of the brightness between the data dn and the data d (n−2) is more than or equal to the threshold value DTH and the data dn is the error data. Thus, it goes on to step S15 and the data d (n−2) that is the current data with the exception of the first and second brightness data is the data of the processed B-flow frame data FFD.

Also in the second variation embodiment, the processed B-flow frame data generation device 63 performs the processes of the steps S11 through S15 for the data of respective pixels and generates the processed B-flow frame data FFDn. In the steps S11 through S15, when the data dn that is the data of the current frame is not the estimated error data (the first and second brightness data), the data dn of the current frame is used as the data for the processed B-flow frame data FFDn so that the current data with the exception of the error data is used. Meanwhile, when the data dn is the estimated error data, the data of the current frame with the exception of the estimated error frame (data dn in FIG. 11 and data d (n−1) in FIG. 12) is used for the processed B-flow frame data FFDn so that the current data with the exception of the error data is used. Thus, the processed B-flow frame data FFDn generated by processing the step S11 through S15 is also the data using the current data with the exception of the error data.

Even if the number of high brightness frames increases, when the number of estimated error data is one, there is a high possibility that the determination whether data is the error data or not is performed based on the high brightness data as the standard data. Thus, there is a possibility that a data that is not supposed to be used as the error data may be used for the processed B-flow frame data FFD. However, in the second variation embodiment, the first and second brightness data are used as the estimated error data and data for two frames are exempt for the standard data. The determination whether a data is the error data or not is performed based on such standard data so that even the number of high brightness frames increases, the data that is not to be used of the error data being used for the processed B-flow frame data FFD can be eliminated. Therefore, display of images momentarily showing high brightness can be prevented more efficiently.

From the above-mentioned explanation, when images momentarily showing high brightness are displayed, the operator controls the number of the estimated error data and prevents images from displaying momentary high brightness.

In the step S15 of the second variation embodiment, when the data dn is the error data as shown in FIG. 12, the data d (n−1) that is the second brightness data can be determined whether or not the data is the error data that is brighter with the predetermined brightness than the data d (n−2) that is the standard data. When the data d (n−1) is the error data, the data d (n−2) that is the current data with the exception of the error data is the processed B-flow frame data FFDn. Meanwhile, when the data d (n−1) is not the error data, the data d (n−1) is used as the processed B-flow frame data FFDn. According to that, the processed B-flow frame data FFD using the current frame data with the exception of the error data can be generated.

Next, the third variation embodiment is explained. The blood flow image is not limited to the B-flow image, and a color Doppler image or a power Doppler image can be applied. When the blood flow image is a color Doppler image, in order to prevent images displaying momentary high blood speed or high power in the color Doppler image, in a plurality of Doppler frame data at different time phases, a processed Doppler frame data using the current data with the exception of the error data that has a faster blood speed or a higher power than the standard data from pixel data corresponding to each other is generated. Then, a color Doppler image based on the processed Doppler frame data is displayed. Note that the Doppler frame data and the processed Doppler frame data include data of blood speed and/or blood flow power generated by the echo signal that is Doppler-processed. When the blood flow image is the color Doppler image as described above, the estimated error data and the error data are determined by using the blood flow or the blood flow power instead of the brightness as a standard, and the processed Doppler frame data is generated as described above. That is, for the above-mentioned estimated error data, the maximum blood speed data or a plurality of data in descending order of blood speed is used instead of the maximum brightness data or a plurality of data in descending order of brightness, then the error data as described above is determined and the processed Doppler frame data is generated. Or, as the estimated data, the maximum blood flow power data or a plurality of data in descending order of blood flow power is used instead of the maximum brightness data or a plurality of data in descending order of brightness, then the error data as described above is determined and the processed Doppler frame data is generated.

When the blood flow image is a power Doppler image, in order to prevent images from displaying momentary high power in the power Doppler image, in a plurality of Doppler frame data at different time phases, a processed Doppler frame data using the current data with the exception of the error data that has a higher blood flow power than the standard data from pixel data corresponding to each other is generated. In this case, the estimated error data and the error data are determined based on criteria of the blood flow power instead of the brightness, and the processed Doppler frame data is generated like above.

Second Embodiment

Next, a second embodiment is explained. Only configuration and operation different from the first embodiment are explained below.

In this embodiment, the processed B-flow frame data generation device 63 generates the processed B-flow frame data FFD for each frame using data that the brightness is the central data of the pixel data corresponding each other in a plurality of B-flow frame data ffd at different time phases.

Figure 13:
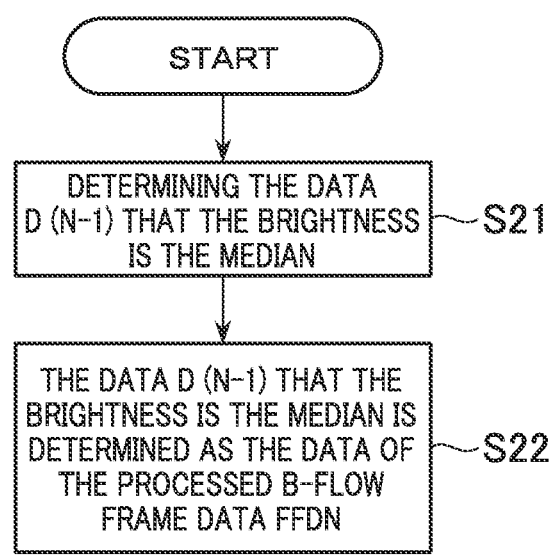
FIG. 13 is a flow chart showing the process for generating the processed B-flow frame data in the second embodiment.

For the generation of the processed B-flow frame data FFD in the present embodiment is explained based on the flow chart in FIG. 13. Here, B-flow frame data ffdn, ffd (n−1), ffd (n−2) of the frame Fn, F (n−1), F (n−2) are objects for processing of steps S21 and S22 in FIG. 13, and display on the frame Fn is explained.

Figure 14:
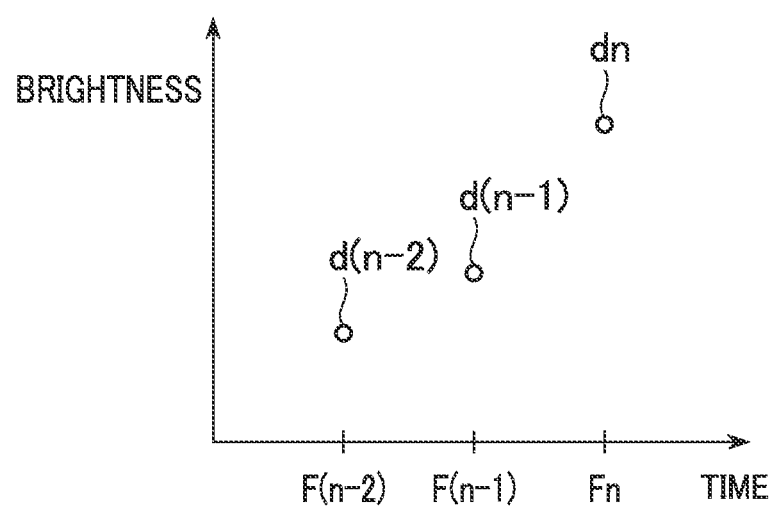
FIG. 14 is a figure for explaining the process of generating the processed B-flow frame data based on the B-flow frame data, which is an example of brightness of pixel data corresponding each other in the B-flow frame data for the three frames in the second embodiment.

First in step S21, the processed B-flow frame data generation device 63 determines the data have a brightness that is the median of the pixel data corresponding to each other in the B-flow frame data ffdn, ffd (n−1), ffd (n−2). For example, as shown in FIG. 14, when the brightness is descended in order for the data dn, d (n−1), d (n−2), the processed B-flow frame data generation device 63 determines the data d (n−1) as the data that the brightness is the median.

Next in step S22, the processed B-flow frame data generation device 63 determines the data d (n−1) as the processed B-flow frame data FFDn for the frame Fn. Then, the processed B-flow frame data generation device 63 performs the steps S21 and S22 for data of respective pixels and generates the processed B-flow frame data FFDn.

According to the present embodiment, the B-flow image generated based on the processed B-flow frame data using the data having the brightness that is the median is displayed. Thus, like the first embodiment, it prevents images from displaying momentary high brightness, and an easily viewed image can be displayed.

Next, a variation embodiment of the second embodiment is explained. In this embodiment, the blood flow image can be a color Doppler image or a power Doppler image. When the blood flow image is a color Doppler image, in a plurality of Doppler frame data at different time phases, the median is determined based on the blood speed or the blood flow power instead of the brightness to generate the processed Doppler frame data. Then the color Doppler image based on the processed Doppler frame data is displayed. When the blood flow image is a power Doppler image, in a plurality of Doppler frame data at different time phases, the median is determined based on the blood flow power instead of the brightness to generate the processed Doppler frame data. Then the power Doppler image based on the processed Doppler frame data is displayed.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic diagnosis apparatus comprising:
   a frame data generation device configured to generate frame data of a blood flow image based on echo signals obtained by transmissions and receptions of ultrasonic waves on a same acoustic ray;
   a processed frame data generation device configured to generate processed frame data for pixel data associated with the frame data, the processed frame data generated using current data excluding error data having a higher brightness, a faster blood speed, or a higher blood flow power than a brightness, a blood speed, or a blood flow power of standard data within pixel data corresponding to each other in at least three consecutive frame data at different time phases, wherein the standard data is a maximum brightness data of the frame data subtracted from the current data; and an image display control device configured to display a blood flow image based on the processed framed data.

2. The ultrasonic diagnosis apparatus of claim 1, wherein the processed frame data generation device is configured to determine a maximum brightness data or a predetermined number of data in descending order of brightness as an estimated error data, and to select the standard data from a data excluding the estimated error data.

3. The ultrasonic diagnosis apparatus of claim 2, wherein the error data including a higher brightness data with a predetermined brightness that is higher than the brightness of the standard data in the estimated error data.

4. An ultrasonic diagnosis apparatus comprising:
a frame data generation device configured to generate frame data of a blood flow image based on echo signals obtained by transmissions and receptions of ultrasonic waves on a same acoustic ray;
a processed frame data generation device configured to generate processed frame data based on the frame data; and an image display control device configured to display a blood flow image based on the processed framed data, wherein the processed frame data generation device is configured to:

determine a maximum brightness data or a predetermined number of data in descending order of brightness as estimated error data of pixel data corresponding to each other in at least three consecutive frame data at different time phases;

use a data of a current frame as the processed frame data when the estimated error data is not the data of the current frame; and generate the processed frame data using the data of the current frame excluding error data that is brighter than a brightness of a standard data of the estimated error data when the estimated error data is the data of the current frame, wherein the standard data is the maximum brightness data of the frame data subtracted from the data of the current frame.

5. The ultrasonic diagnosis apparatus of claim 4, wherein the error data includes a higher brightness data with a predetermined brightness that is higher than the brightness of the standard data in the estimated error data.

* * * * *